(12) United States Patent
Fehr et al.

(10) Patent No.: US 7,589,055 B2
(45) Date of Patent: Sep. 15, 2009

(54) COMPOUNDS FOR A CONTROLLED RELEASE OF ACTIVE MOLECULES

(75) Inventors: Charles Fehr, Versoix (CH); José Galindo, Grand-Saconnex (CH); Arnaud Struillou, Archamps (FR)

(73) Assignee: Firmenich SA, Geneva (CH)

( * ) Notice: Subject to any disclaimer, the term of this patent is extended or adjusted under 35 U.S.C. 154(b) by 587 days.

(21) Appl. No.: 11/245,671

(22) Filed: Oct. 6, 2005

(65) Prior Publication Data

US 2006/0040848 A1 Feb. 23, 2006

Related U.S. Application Data

(63) Continuation of application No. PCT/IB2004/001605, filed on May 10, 2004.

(30) Foreign Application Priority Data

Jun. 2, 2003 (WO) ..................... PCT/IB03/02415

(51) Int. Cl.
*A23L 1/226* (2006.01)
(52) U.S. Cl. ............................. 512/21; 512/25; 252/522
(58) Field of Classification Search ................... 512/25, 512/21; 252/522
See application file for complete search history.

(56) References Cited

U.S. PATENT DOCUMENTS

| 3,506,674 | A | | 4/1970 | Berger et al. ............. 260/294.8 |
| 3,900,520 | A | | 8/1975 | Schenk et al. ............... 260/586 |
| 3,979,422 | A | | 9/1976 | Schenk et al. ........... 260/455 R |
| 4,107,209 | A | * | 8/1978 | Wilson et al. ................. 568/42 |
| 4,154,693 | A | * | 5/1979 | Wilson et al. ............... 510/106 |
| 4,162,335 | A | * | 7/1979 | Wilson et al. ............... 426/535 |
| 4,209,025 | A | | 6/1980 | Wilson et al. ............. 131/17 R |
| 2003/0119712 | A1 | * | 6/2003 | Fehr et al. ...................... 512/1 |

FOREIGN PATENT DOCUMENTS

GB 1 602 747 11/1981

* cited by examiner

*Primary Examiner*—David Wu
*Assistant Examiner*—M. Reza Asdjodi
(74) *Attorney, Agent, or Firm*—Winston & Strawn LLP

(57) ABSTRACT

The present invention relates to the field of perfumery. More particularly, it concerns compounds comprising at least one β-carbonate or β-thio carbonyl moiety capable of liberating a perfuming molecule such as, for example, an α,β-unsaturated ketone, aldehyde or carboxylic ester. The present invention concerns also the use of said compounds in perfumery as well as the perfuming compositions or perfumed articles comprising the invention's compounds.

9 Claims, No Drawings

COMPOUNDS FOR A CONTROLLED RELEASE OF ACTIVE MOLECULES

CROSS-REFERENCE TO RELATED APPLICATIONS

This application is a continuation of International application PCT/IB2004/001605 filed 10 May 2004 the entire content of which is expressly incorporated herein by reference thereto.

TECHNICAL FIELD

The present invention relates to the field of perfumery. More particularly, it concerns compounds comprising at least one β-carbonate or β-thio carbonyl moiety capable of liberating an active molecule such as, for example, an α,β-unsaturated ketone, aldehyde or carboxylic ester.

BACKGROUND

The perfume industry has a particular interest for compounds which are capable of prolonging the effect of active ingredients over a certain period of time, for example in order to overcome the problems encountered when using perfuming ingredients which are too volatile or have a poor substantivity. These compounds can be used in various applications, as for example in fine or functional perfumery. The washing of textiles is a particular field in which there is a constant quest to enable the effect of active substances, in particular perfumes, to be effective for a certain period of time after washing and drying. Indeed, many substances having odors which are particularly suitable for this type of application are, in fact, known to lack tenacity on laundry, or do not remain on the laundry when rinsed, with the result that their perfuming effect is experienced only briefly and not very intensely. Given the importance of this type of application in the perfume industry, research in this field has been sustained, in particular with the aim of finding new, and more effective solutions to the aforementioned problems.

To the best of our knowledge, none of the compounds of the present invention are known from the prior art.

SUMMARY OF THE INVENTION

The present invention now relates to compounds comprising at least one β-carbonate or β-thio carbonyl moiety capable of liberating an active molecule such as a fragrance. Other aspects of the invention are the use of said compounds as perfuming ingredients as well as the perfuming compositions or perfumed articles comprising the invention's compounds.

DETAILED DESCRIPTION OF THE PREFERRED EMBODIMENTS

We have, surprisingly, discovered that the above-mentioned problem can be solved by using compounds comprising at least one β-carbonate or β-thio carbonyl moiety capable of liberating an active enone.

As "active enone" we mean here, for example, an α,β-unsaturated ketone, aldehyde or carboxylic ester capable of bringing an odor benefit or effect into its surrounding environment, such as a perfuming ingredient. By "perfuming ingredient" it is meant here a compound, which is of current use in perfumery industry, i.e. a compound which is used as ingredient in perfuming preparations or compositions in order to impart an hedonic effect.

The compounds of the present invention are of formula $$P-X-R \quad (I)$$

wherein:
a) P represents a radical derived from a perfuming α,β-unsaturated ketone, aldehyde or carboxylic ester and is represented by formula

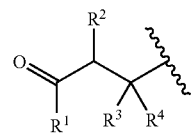

(II)

in which $R^1$ represents a hydrogen atom, a $C_1$ to $C_6$ alkoxyl radical or a $C_1$ to $C_{15}$ linear, cyclic or branched alkyl, alkenyl or alkadienyl radical, optionally substituted by up to four $C_1$ to $C_4$ alkyl groups; and $R^2$, $R^3$ and $R^4$ represent a hydrogen atom, an aromatic ring or a $C_1$ to $C_{15}$ linear, cyclic or branched alkyl, alkenyl or alkadienyl radical, optionally substituted by up to four $C_1$ to $C_4$ alkyl groups; two, or three, of the groups $R^1$ to $R^4$ can be bonded together to form a saturated or unsaturated ring having 6 to 20 carbon atoms and including the carbon atom to which said $R^1$, $R^2$, $R^3$ or $R^4$ groups are bonded, this ring being optionally substituted by up to four $C_1$ to $C_4$ linear or branched alkyl or alkenyl groups or by one $C_3$ to $C_9$ cyclic alkyl or alkenyl group; and b) X represents a sulfur atom and R represents a cyclic, linear or branched alkyl, alkenyl or alkadienyl $C_1$-$C_5$ hydrocarbon radical substituted with a $Si(OR^5)_3$ group, $R^5$ representing a $C_1$-$C_5$ alkyl or alkenyl group; or X represents a OC(O)O functional group and R represents a cyclic, linear or branched alkyl, alkenyl or alkadienyl $C_1$-$C_5$ hydrocarbon radical optionally substituted with a $Si(OR^5)_3$ group, $R^5$ representing a $C_1$-$C_5$ alkyl or alkenyl group.

A compound of formula (I) can be in the form of a pure diastereomer or stereoisomer or in the form of any mixture of said isomers.

In general, said perfuming α,β-unsaturated ketone, aldehyde or carboxylic ester, which is susceptible of being generated from P as will be explained further below, is a compound having from 8 to 20 carbon atoms, or even more preferably between 10 and 15 carbon atoms.

According to a particular embodiment of the invention, examples of P radicals are of the formulae (P-1) to (P-12)

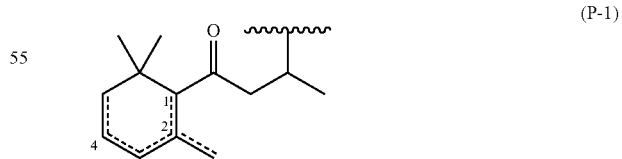

(P-1)

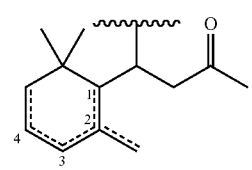

(P-2)

-continued

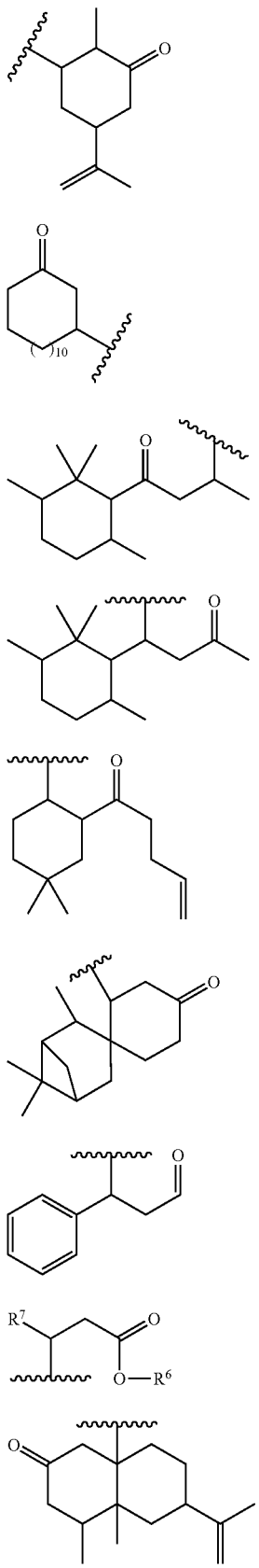

(P-3)

(P-4)

(P-5)

(P-6)

(P-7)

(P-8)

(P-9)

(P-10)

(P-11)

-continued

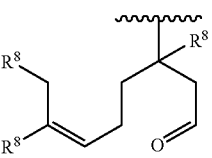

(P-12)

in the form of any one of their isomers, and wherein the dotted lines represent a single or double bond, $R^6$ represents a methyl or ethyl group, $R^7$ represents a $C_6$ to $C_9$ linear or branched alkyl, alkenyl or alkadienyl group and $R^8$ represents a hydrogen atom or a methyl group.

The radicals of the formulae (P-1) to (P-12) may be in the form of pure diastereomers or stereoisomers or in the form of any mixture of said isomers. Preferably said radicals are in a form which allows to obtain the active enone in the desired configuration. For example, if it is desired to release trans-delta damascone, then the corresponding radical (P-1) will be in a form wherein the methyl substituents of the cyclohexyl and the ketone groups are in a trans configuration.

Preferred compounds of formula (I) are those wherein X represents a OC(O)O functional group, R represents a linear or branched alkyl or alkenyl $C_2$-$C_5$ hydrocarbon radical and P represents a radical of the formulae (P-1) to (P-12) as defined above.

In a more preferred embodiment of the invention the compounds of formula (I) are those wherein X represents a OC(O)O functional group, R represents a linear or branched alkyl $C_2$-$C_5$ hydrocarbon radical and P represents a radical of the formulae (P-1) to (P-7) as defined above The compounds of formula (I) may be synthesized from commercially available compounds using conventional methods. The invention's compounds wherein X represents a sulfur atom are obtainable by the [1,4]-addition reaction between a thiol of formula HSR and a perfuming α,β-unsaturated ketone, aldehyde or carboxylic ester of formula (II')

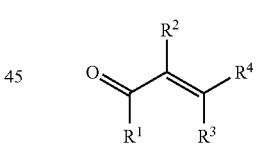

(II')

R, $R^1$, $R^2$, $R^3$ and $R^4$ having the meaning indicated in formula (I) and the configuration of the carbon-carbon double bond in formula (II') can be of the E or Z type.

The invention's compounds wherein X represents a OC(O)O functional group may be more advantageously obtained by the reaction between a compound of formula ClC(O)OR and a compound of formula (II''), which is the aldol derivative of the odoriferous compound of formula (II'),

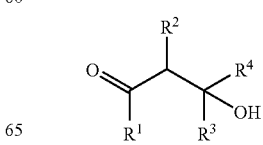

(II'')

R, $R^1$, $R^2$, $R^3$ and $R^4$ having the meaning indicated in formula (I).

Although it is not necessary to provide an exhaustive list of the compounds of formula HSR or ClC(O)OR which may be used in the synthesis of the invention's compounds, one can cite as preferred examples ethyl, butyl or pentyl chloroformate or 3-(triethoxysilyl)-1-propanethiol.

Although, it is not possible to provide an exhaustive list of the currently known odoriferous compounds of formula (II') which can be used in the synthesis of the invention's compounds, and subsequently be released, the following can be named as preferred examples: alpha-damascone, (−)-alpha-damascone, beta-damascone, gamma-damascone, delta-damascone, trans- delta-damascone, alpha-ionone, beta-ionone, gamma-ionone, delta-ionone, beta-damascenone, 3-methyl-5-propyl-2-cyclohexen-1-one, 1(6),8-P-menthadien-2-one, 2,5-dimethyl-5-phenyl-1-hexen-3-one, 1-(5,5-dimethyl-1-cyclohexen-1-yl)-4-penten-1-one, 8 or 10-methyl-alpha-ionone, 2-octenal, 1-(2,2,3,6-tetramethyl - 1-cyclohexyl)-2-buten-1-one, 4-(2,2,3,6-tetramethyl-1-cyclohexyl)-3-buten-2-one, 2-cyclopentadecen-1-one, nootkatone, cinnamic aldehyde, 2,6,6-trimethyl -bicyclo[3.1.1]heptane-3-spiro-2'-cyclohexen-4'-one, ethyl 2,4-deca-dienoate, ethyl 2-octenoate, methyl 2-nonenoate, ethyl 2,4-undecadienoate and methyl 5,9-dimethyl-2,4,8-decatrienoate. Of course, the aldol derivatives of formula (II'') of the above-mentioned compounds (II') are also useful in the synthesis of the invention's compounds.

Amongst the odoriferous compounds cited in the list hereinabove, the preferred are: the damascones, ionones, beta-damascenone, 1-(5,5-dimethyl-1-cyclohexen-1-yl)-4-penten-1-one, 1 (6),8-P-menthadien-2-one, 2-cyclopentadecen-1-one, 1-(2,2,3,6-tetramethyl-1-cyclohexyl)-2-buten-1-one, 4-(2,2,3,6-tetramethyl-1-cyclohexyl)-3-buten-2-one and 2-cyclopentadecen-1-one.

As can be noticed from formula (I), the compounds of the invention are composed of two main parts, namely the release moiety P—X and the terminal group R.

Owing to the particular chemical structure of the release moiety P—X, the compounds of formula (I) are capable of releasing, via a decomposition reaction, a residue and a perfuming α,β-unsaturated ketone, aldehyde or carboxylic ester of formula (II').

An example of said decomposition reaction is illustrated in the following scheme:

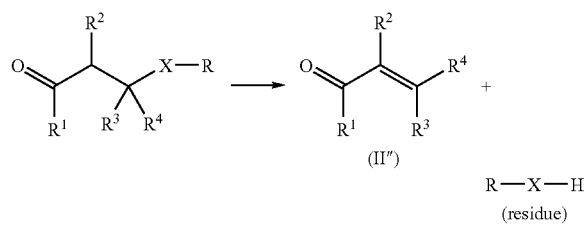

The compound R—X—H, which is also the residue of the decomposition reaction, may further decompose into other chemical compounds which may be odorless or possess an odor; preferably said residue, as well as its possible decomposition compound, is an odorless compound. Similarly, the compound of formula (I) is preferably odorless.

The nature of X plays an important role in the release kinetics of the odoriferous molecule. Thus, by a careful choice of the nature of X it is possible to tune the perfume release properties of the compounds of formula (I).

The second component of the compounds of the invention is the terminal group R. Said group can have an influence in the releasing properties of the compounds of formula (I). Indeed, a shrewd choice of the chemical nature of said fragment, e.g. the length or the degree of branching, can allow to fine tune the perfume releasing properties. Moreover, depending on its specific nature, it can also play an important role in the effective deposition and surface substantivity of the molecules of the invention on the surface used for the application, especially on fabrics and hair.

The decomposition reaction, which leads to the release of the active enone, is believed to be influenced by pH changes or heat, but may be triggered by other types of mechanisms.

As the compounds of the invention are useful ingredients for the perfuming of various products, the present invention concerns also all perfuming compositions comprising the invention's compounds, said compositions being useful perfuming ingredients.

Therefore, another object of the present invention is a perfuming composition comprising:
i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxy-ethoxy)-1-ethanol or ethyl citrate, which are the most commonly used.

As solid carrier one may cite, as non-limiting examples, an absorbing gum or polymer, or yet an encapsulating material; said materials are well known to a person skilled in the art.

Generally speaking, by "perfumery base" we mean here a composition comprising at least one perfuming co-ingredient.

Said perfuming co-ingredient is not of the formula (I). Moreover, by "perfuming co-ingredient" it is meant here a compound, which is used in perfuming preparation or composition to impart an hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, aldehydes, ketones, esters, ethers, acetates, nitrites, terpene hydrocarbons, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

For the compositions which comprise both a perfumery carrier and a perfumery base, other suitable perfumery carrier than those previously specified can also be ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

Generally speaking, by "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

As previously mentioned, a compound of formula (I), or a composition containing at least one compound (I), is a useful perfuming ingredient which can be advantageously used in all the fields of modern perfumery, such as fine perfumery or functional perfumery, as it enables a controlled release of odoriferous molecules.

Indeed, the invention's compounds may be advantageously employed in fine or functional perfumery to achieve a more controlled deposition and/or release, of odoriferous compounds. For example, perfuming ingredients present as such in washing or perfuming compositions can have little staying-power on a surface and consequently be often eliminated, for example in the rinsing water or upon drying of said surface. This problem can be solved by using a compound of formula (I), for which we have been able to show that it possesses a surprising stability over storage and staying-power or tenacity on surfaces, such as textiles. Therefore, the compounds according to the invention, owing to a good substantivity, a low volatility and a controlled release of odoriferous molecules, can be incorporated in any application requiring the effect of rapid or prolonged liberation of an odoriferous component as defined hereinabove and furthermore can impart a fragrance and a freshness to a treated surface which will last well beyond the rinsing and/or drying processes. Suitable surfaces are, in particular, textiles, hard surfaces, hair and skin.

Thus, in perfumery, one of the major advantages of the invention resides in the fact that the compounds of formula (I) impart an intense fragrance to the treated surface, produced by an odoriferous enone, which would not be detected on said surface over a sufficiently long period if the α,β-unsaturated carbonyl derivative of formula (II') had been used as such, i.e. without a precursor.

Such a behavior makes the compounds of formula (I) particularly suitable as precursors of perfuming ingredients for applications associated with functional or fine perfumery. Consequently, the use of an invention's compound as perfuming ingredient is another object of the present invention. In other words, a method to confer, enhance, improve or modify the odor properties of a perfuming composition or of a perfumed article, which method comprises adding to said composition or article an effective amount of at least a compound of formula (I).

Furthermore, the invention's compound can also be advantageously used in all the fields of modern perfumery to positively impart or modify the odor of a consumer product into which said compound (I) is added. Consequently, a perfumed article comprising:

i) as perfuming ingredient, at least one compound of formula (I) or an invention's composition; and ii) a consumer product base is also an object of the present invention.

For the sake of clarity, it has to be mentioned that, by "consumer product base" we mean here a consumer product which is compatible with perfuming ingredients. In other words, a perfumed article according to the invention comprises the functional formulation, as well as optionally additional benefit agents, corresponding to a consumer product, e.g. a detergent or an air freshener, and an olfactive effective amount of at least one invention's compound.

The nature and type of the constituents of the consumer product base do not warrant a more detailed description here, which in any case would not be exhaustive, the skilled person being able to select them on the basis of its general knowledge and according to the nature and the desired effect of said article.

Suitable consumer products comprise solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or antiperspirants, air fresheners and also cosmetic preparations. As detergents are intended applications such as detergent compositions or cleaning products for washing up or for cleaning various surfaces, e.g. intended for textile, dish or hard-surface treatment, whether they are intended for domestic or industrial use. Other perfumed articles are fabric refreshers, ironing waters, papers, wipes or bleaches.

Preferred consumer products are perfumes, fabric detergents or softener bases.

Typical examples of fabric detergents or softener compositions into which the compounds of the invention can be incorporated are described in WO 97/34986 or in U.S. Pat. Nos. 4,137,180 and 5,236,615 or EP 799 885. Other typical detergent and softening compositions which can be used are described in works such as Ullman's Encyclopedia of Industrial Chemistry, vol. A8, pages 315-448 (1987) and vol. A25, pages 747-817 (1994); Flick, Advanced Cleaning Product Formulations, Noye Publication, Park Ridge, N.J. (1989); Showell, in Surfactant Science Series, vol. 71: Powdered Detergents, Marcel Dekker, New York (1988); Proceedings of the World Conference on Detergents (4th, 1998, Montreux, Switzerland), AOCS print.

Some of the above-mentioned articles may represent an aggressive medium for the invention's compounds, so that it may be necessary to protect the latter from premature decomposition, for example by encapsulation.

The proportions in which the compounds according to the invention can be incorporated into the various aforementioned articles or compositions vary within a wide range of values. These values are dependent on the nature of the article or product to be perfumed and on the desired olfactory effect as well as the nature of the co-ingredients in a given composition when the compounds according to the invention are mixed with perfuming co-ingredients, solvents or additives commonly used in the art.

For example, typical concentrations are in the order of 0.001% to 5% by weight, or even more, of the compounds of the invention based on the weight of the composition into which they are incorporated. Concentrations lower than these, such as in the order of 0.01% to 1% by weight, can be used when these compounds are applied directly in the perfuming of the various consumer products mentioned hereinabove.

EXAMPLES

Another object of the present invention relates to a method for the perfuming of a surface or to a method for intensifying or prolonging the diffusion effect of the characteristic fragrance of an odoriferous ingredient on a surface, characterized in that said surface is treated in the presence of a compound of formula (I). Suitable surfaces are, in particular, textiles, hard surfaces, hair and skin.

EXAMPLES

The following examples are illustrative of the present invention's embodiments, and further demonstrate the advantages of the present invention relative to the prior art teachings. In the following examples the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical displacement $\delta$ are indicated in ppm with respect to the TMS as standard, the coupling constants J are expressed in Hz.

Example 1

Synthesis of Compounds of Formula (I)

a) Synthesis of 4,4-dimethyl-2-(4-pentenoyl)cyclohexyl ethyl carbonate

A solution of ethyl chloroformate (1.5 g, 13.8 mmoles) in $CH_2Cl_2$ (3 ml) was added dropwise, over 15 minutes, to a stirred solution of 1-(2-hydroxy-5,5-dimethyl-1-cyclohexyl)-4-penten-1-one (1.6 g, 7.6 mmoles), $NEt_3$ (1.4 g, 13.8 mmoles) and dimethylaminopyridine (1.0 g, 8.2 mmoles) in $CH_2Cl_2$ at 3-6° C. under nitrogen. The mixture was allowed to attain room temperature and stirred overnight. The mixture was then poured into a solution of cold 37% aqueous HCl (2 ml) in water (25 ml) and extracted with $Et_2O$. The organic phase was washed with saturated aqueous $NaHCO_3$ and saturated aqueous NaCl, and dried over anhydrous $Na_2SO_4$.

Filtration, concentration and chromatography (Silica, cyclohexane/EtOEt: 93/7) afforded the title compound as a pale yellow oil (1.85 g, yield=86%)

$^1$H-NMR: 0.92 (s, 3H); 1.01 (s, 3H); 1.20 (m, 1H); 1.29 (t, J=7, 3H); 1.42 (m, 1H); 1.50 (m, 1H); 1.70 (m, 1H); 1.77 (t, J=7, 1H); 1.95 (m, 1H); 2.30 (2xt, J=7.7, 2H); 2.48-2.68 (m, 3H); 4.16 (m, 2H); 4.96 (m, 1H); 5.02 (m, 1H); 5.32 (m, 1H); 5.79 (m, 1H). $^{13}$C-NMR: 209.1 (s); 154.6 (s); 137.3 (d); 115.1 (t); 72.5 (d); 63.9 (d); 49.3 (d); 39.8 (t); 34.6 (t); 32.7 (q); 32.4 (t); 29.9 (s); 27.6 (t); 26.6 (t); 23.9 (q); 14.2 (q).

b) Synthesis of 3-{[3-(triethoxysilyl)propyl]thio}-1-(2,6,6-trimethyl-2-cyclohexen-1-yl)-1-butanone A solution of α-damascone (9.60 g; 50.0 mmol) and 3-mercaptopropyltriethoxysilane (95% pure, 12.52 g, 50.0 mmol) in THF (40 ml) was treated with DBU (1.52 g, 10.0 mmol) and stirred at 40° C. for 90 min. The reaction solution was treated with 5% HCl, extracted twice with ether, washed with water, saturated aqueous $NaHCO_3$ and then with saturated aqueous NaCl, dried over $Na_2SO_4$ and concentrated at 70° C./0.01 mbar. The reaction yielded 21.2 g (99%). of crude product:

$^1$H-NMR: 0.74 (m, 2H); 0.91 (s, 3H); 0.93 (s, 3H); 1.22 (t, J=7, 9H); 1.28 (t, J=7, 3H); 1.60 (bs, 3H); 1.71 (m, 4H); 2.00-2.18 (m, 2H); 2.50-2.95 (m, 5H); 3.28 (m, 1H); 3.82 (q, J=7, 6H); 5.58 (b, 1H). $^{13}$C-NMR: 211.1 (s); 130.0 (s); 123.7 (d); 63.6 (d); 58.4 (t); 53.3 (t); 34.3 (d); 33.95 (t); 32.45 (s); 30.8 (t); 28.0 (q); 27.8 (q); 23.5 (q); 23.4 (t); 22.6 (t); 21.65 (q); 18.3 (t); 10.1 (t).

c) Synthesis of ethyl trans-1-methyl-3-oxo-3-(2,6,6-trimethyl-3-cyclohexen-1-yl)propyl carbonate The starting material, namely the 3-hydroxy-1-(2,6,6-trimethyl-3-cyclohexen-1-yl)-1-butanone, was obtained according to U.S. Pat. No. 4,334,098.

A solution of 3-hydroxy-1-(2,6,6-trimethyl-3-cyclohexen-1-yl)-1-butanone (2.00 g, 84% pure, 8.0 mmol) in pyridine (1.85 g, 23.4 mmol) was treated at 0° C. with ethyl chloroformate (1.24 g, 23.4 mmol). The reaction solution was stirred at room temperature for 36 hours, treated with aqueous 5% HCl and extracted twice with ether, washed with water, saturated aqueous $NaHCO_3$, then with saturated aqueous NaCl, dried over $Na_2SO_4$ and concentrated. The oil thus obtained was purified by flash-chromatography (cyclohexane/AcOEt=98:2), using $SiO_2$ (100 g). Yield: 2.06 g (78%).

$^1$H-NMR: 0.89 (d, J=7, 3H); 0.92-1.03 (4 s, 6H); 1.23-1.37 (m, 6H); 1.70 (m, 1H); 1.96 (m, 1H); 2.18-2.28 (m, 1H); 2.50 (m, 1.5H); 2.67 (m, 0.5H); 2.87 (m, 0.5H); 3.03 (m, 0.5H); 4.18 (m, 2H); 5.21 (m, 1H); 5.42-5.48 (m, 1H); 5.54 (m, 1H). $^{13}$C-NMR: 211.4 (s); 154.4 (s); 131.7 (d); 124.2 (d); 70.5 (d); 63.8 (t); 63.1 (d); 53.1 (t); 41.7 (t); 33.1 (s); 31.6 (d); 29.7 (q); 20.7 (q); 20.0 (q); 19.8 (q); 14.3 (q).

d) Synthesis of 4-{[3-(trimethoxysilyl)propyl]thio}-4-(2,6,6-trimethyl-1-cyclohexen-1-yl)-2-butanone To a well-stirred mixture of β-ionone (10.00 g, 52.1 mmol) and DBU (79 mg, 0.52 mmol (1 mol-%)) was rapidly added 3-mercaptopropyltrimethoxysilane (10.21 g, 52.1 mmol) at 25-30° C. After 72 hours, the reaction mixture was poured onto a cold stirred 5% aqueous HCl solution and extracted twice with $Et_2O$. The organic phases were washed (H2O, saturated aqueous $NaHCO_3$ and brine), dried ($Na_2SO_4$), filtered and concentrated. The crude extract was dried for 1 hour at 65-70° C./0.01 Torr to give 18.00 g of the title thioether containing approximativaly 10% of β-ionone. Yield: 80%.

$^1$H-NMR: 0.74 (dt, J=3.5 and 8.5, 2H); 0.94 (s, 3H); 1.15 (s, 3H); 1.35-1.74 (m, 6H); 1.80 (s, 3H); 1.91 (m, 2H); 2.17 (s, 3H); 2.58 (m, 2H); 2.88 (dd, J=3.5 and 18.0, 1H); 3.28 (dd, J=8.0 and 18.0, 1H); 3.56 (s, 9H); 3.99 (dd, J=3.5 and 8.0, 1H). $^{13}$C-NMR: 206.6 (s); 139.9 (s); 131.6 (s); 53.2 (t); 50.5 (q); 39.8 (t); 38.1 (d); 37.0 (t); 35.8 (s); 33.7 (t); 30.7 (q); 28.3 (q); 27.9 (q); 22.8 (t); 22.4 (q); 19.3 (t); 8.8 (t).

e) Synthesis of 4-{[3-(trimethoxysilyl)propyl]thio}-4-(2,6,6-trimethyl-2-cyclohexen-1-yl)-2-butanone To a stirred solution of α-ionone (1.92 g, 10.0 mmol) and 3-mercaptopropyl-trimethoxysilane (1.96 g, 10.0 mmol) at 12° C. was rapidly added DBU (0.14 ml, 152 mg, 1.0 mmol). The temperature rose to 19° C. and the solution turned orange. After 135 minutes at 20° C, the reaction mixture was poured onto a cold stirred 5% aqueous HCl solution and extracted twice with $Et_2O$. The organic phases were washed ($H_2O$, saturated aqueous $NaHCO_3$ and brine), dried ($Na_2SO_4$), filtered and concentrated. The crude extract was dried for 1 hour at 65-70° C./0.01 Torr to give 2.77 g of the title thioether (71%).

MS: 330 (1), 265 (5), 233 (42), 191 (58), 136 (34), 121 (100), 93 (55), 91 (42), 77 (21), 43 (42). $^1$H-NMR: 0.74 (m, 2H); 0.90 (s, 3H); 1.01 (s, 3H); 1.14 (m, 1H); 1.28 (m, 1H); 1.70 (m, 2H); 1.80 (broad s, 3H); 1.90-2.00 (m, 3H); 2.14 (s, 3H); 2.50-2.70 (m, 4H); 3.56 (s, 9H); 3.60 (m, 1H); 5.43 (broad, 1H). $^{13}$C-NMR: 207.0 (s); 134.1 (s); 123.2 (d); 55.4 (d); 50.5 (q); 48.7 (t); 38.4 (d); 36.3 (t); 33.5 (s); 31.6 (t); 30.9 (q); 28.6 (q); 27.7 (q); 25.4 (q); 23.0 (t); 22.9 (t); 8.7 (t).

Example 2

A Fabric Softener Base Containing a Compound of Formula (I)

A fabric-softener base was prepared by admixing the following ingredients:

| Ingredients | Parts by weight |
| --- | --- |
| Stepantex VK 90 diester quat[1] | 16.5 |
| Calcium chloride | 0.2 |
| Deionised Water | 81.8 |
| Total | 100 |

[1] origin: Stepan Europe, France

The compound to be tested was added to 35 g of fabric-softener base above in an amount of about 1 mmole. After a vigorous stirring the mixture was poured into the fabric-softener compartment of a Miele Novotronic W900-79 CH washing machine.

Then, 17 small terry towels (18×18 cm, about 30 g each) and 2.3 kg of large cotton towels (11 towels of 50×70 cm) were washed at 40° C. using the short cycle program and 136 g of Henkel "ECE Colour fastness Test Detergent 77" unperfumed detergent.

At the end of the wash, the 17 small terry towels were dried in a drying room for 24 hours and then packed loosely in aluminium foil and evaluated by a 20 people panel 24 hours, 3 days and 7 days after the wash.

Each panelist was asked to rate the various terry towels tested on an intensity scale of 1 to 7 (1: no odor, 2: weak odor, 3: slightly weak odor, 4: medium odor, 5: slightly strong odor, 6: strong odor, 7: very strong odor).

As reference was used a fabric-softener base containing 1 mmole of the corresponding pure perfumery enone which was tested through the same process.

The results are summarized in the following table:

| Tested molecule | Quantity[1] | mmol[2] | Average intensity[3] |
| --- | --- | --- | --- |
| 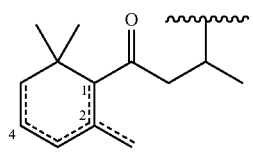 reference | 0.55 | 1.0 | 3.2 |
| 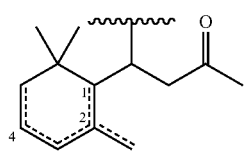 | 0.81 | 1.0 | 5.0 |

[1] quantity added into the 35 g of the fabric-softener base, in parts by weight
[2] millimoles added into the 35 g of the fabric-softener base
[3] average of the odor intensity of the dry fabric in the period ranging from one day to seven days after the wash

What is claimed is:

1. A compound of the formula $$P-X-R \qquad (I)$$

wherein:

a) P represents a radical derived from an perfuming α,β-unsaturated ketone, aldehyde or carboxylic ester and is represented by formula

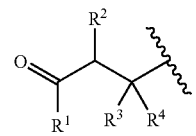

(II)

in which $R^1$ represents a hydrogen atom, a $C_1$ to $C_6$ alkoxyl radical or a $C_1$ to $C_{15}$ linear, cyclic or branched alkyl, alkenyl or alkadienyl radical, optionally substituted by up to four $C_1$ to $C_4$ alkyl groups; and $R^2$, $R^3$ and $R^4$ represent a hydrogen atom, an aromatic ring or a $C_1$ to $C_{15}$ linear, cyclic or branched alkyl, alkenyl or alkadienyl radical, optionally substituted by up to four $C_1$ to $C_4$ alkyl groups; two, or three, of the groups $R^1$ to $R^4$ can be bonded together to form a saturated or unsaturated ring having 6 to 20 carbon atoms and including the carbon atom to which said $R^1$, $R^2$, $R^3$ or $R^4$ groups are bonded, this ring being optionally substituted by up to four $C_1$ to $C_4$ linear or branched alkyl or alkenyl groups or by one $C_3$ to $C_9$ cyclic alkyl or alkenyl groups; and b) X represents a sulfur atom and R represents a cyclic, linear or branched alkyl, alkenyl or alkadienyl $C_1$-$C_5$ hydrocarbon radical wherein the alkyl, alkenyl or alkadienyl $C_1$-$C_5$ hydrocarbon radical is substituted with a $Si(OR^5)_3$ group, $R^5$ representing a $C_1$-$C_5$ alkyl or alkenyl group; or X represents a OC(O)O functional group and R represents a cyclic, linear or branched alkyl, alkenyl or alkadienyl $C_1$-$C_5$ hydrocarbon radical optionally substituted with a $Si(OR^5)_3$ group, $R^5$ representing a $C_1$-$C_5$ alkyl or alkenyl group;

said compound of formula (I) being in the form of a pure diastereomer or stereoisomer or in the form of any mixture of said isomers.

2. A compound according to claim 1, wherein X represents a OC(O)O functional group, R represents a linear or branched alkyl or alkenyl $C_2$-$C_5$ hydrocarbon radical and P represents a radical of the formulae (P-1) to (P-12)

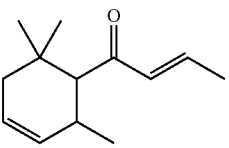

(P-1)

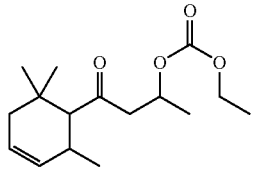

(P-2)

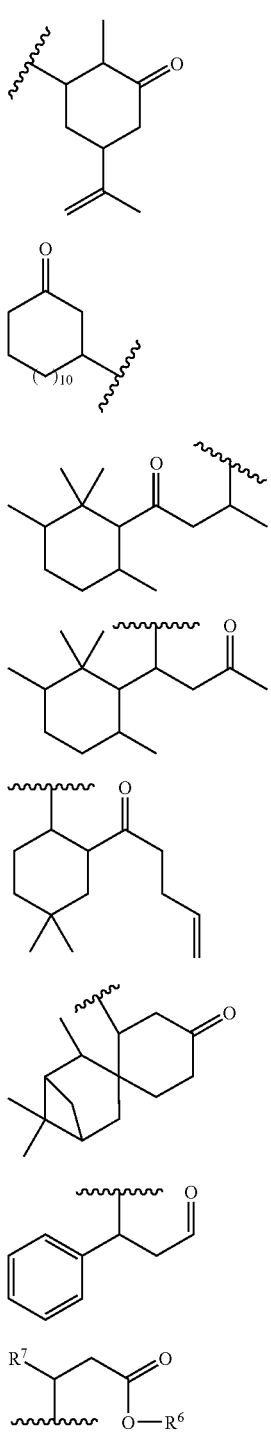

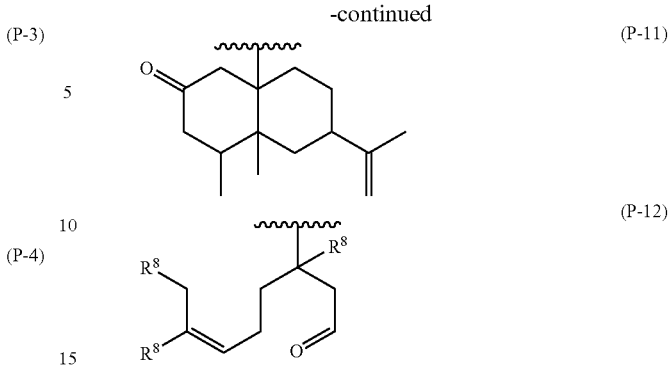

in the form of any one of their isomers, and wherein the dotted lines represent a single or double bond, $R^6$ represents a methyl or ethyl group, $R^7$ represents a $C_6$ to $C_9$ linear or branched alkyl, alkenyl or alkadienyl group and $R^8$ represents a hydrogen atom or a methyl group.

3. A compound according to claim 2, wherein X represents a OC(O)O functional group, R represents a linear or branched alkyl C2-C5 hydrocarbon radical and P represents a radical of the formulae (P-1) to (P-7).

4. A perfuming composition comprising:
  i) as perfuming ingredient, at least one compound of formula (I), as defined in claim 1;
  ii) at least one ingredient selected from the group consisting of a perfumery carrier and a perfumery base; and
  iii) optionally at least one perfumery adjuvant.

5. A method to confer, enhance, improve or modify the odor properties of a perfuming composition or of a perfumed article, which method comprises adding to said composition or article an effective amount of a compound of formula (I), as defined in claim 1.

6. A perfumed article comprising:
  i) as perfuming ingredient, at least one compound of formula (I) as defined in claim 1; and
  ii) a consumer product base.

7. A perfumed article according to claim 6, wherein said consumer product base is in the form of a solid or liquid detergent, a fabric softener, a perfume, a cologne, an aftershave lotion, a perfumed soap, a shower or bath salt, mousse, oil or gel, a hygiene product, a hair care product, a shampoo, a body-care product, a deodorant, a antiperspirant, an air freshener, a cosmetic preparation, a fabric refresher, an ironing water, a paper, a wipe or a bleach.

8. A method for the perfuming of a surface, characterized in that said surface is treated in the presence of a compound of formula (I) as defined in claim 1.

9. A method for intensifying or prolonging the diffusion effect of an odoriferous ingredient on a surface, characterized in that said surface is treated in the presence of a compound of formula (I) as defined in claim 1.

* * * * *

UNITED STATES PATENT AND TRADEMARK OFFICE
CERTIFICATE OF CORRECTION

PATENT NO. : 7,589,055 B2  Page 1 of 1
APPLICATION NO. : 11/245671
DATED : September 15, 2009
INVENTOR(S) : Fehr et al.

It is certified that error appears in the above-identified patent and that said Letters Patent is hereby corrected as shown below:

Column 14:
Line 24 (claim 3, line 3), change "C2-C5" to -- $C_2$-$C_5$ --.

Signed and Sealed this

Twentieth Day of October, 2009

David J. Kappos
*Director of the United States Patent and Trademark Office*